United States Patent [19]

Olsen et al.

[11] Patent Number: 4,617,273
[45] Date of Patent: Oct. 14, 1986

[54] ALPHA-ACETOLACTATE DECARBOXYLASE ENZYME AND PREPARATION THEREOF

[75] Inventors: Frank Olsen, Lyngby; Knud Aunstrup, Fredensborg, both of Denmark

[73] Assignee: Novo Industri A/S, Denmark

[21] Appl. No.: 616,191

[22] Filed: Jun. 1, 1984

[30] Foreign Application Priority Data

Jun. 3, 1983 [DK] Denmark ............................ 2524/83

[51] Int. Cl.$^4$ ........................... C12N 9/88; C12R 1/08; C12R 1/10
[52] U.S. Cl. .................................... 435/232; 435/833; 435/836; 426/12
[58] Field of Search ................. 435/232, 833, 836, 13; 426/12

[56] References Cited

FOREIGN PATENT DOCUMENTS 0046066 2/1982 European Pat. Off. .

OTHER PUBLICATIONS

Stormer, Journal of Biological Chemistry, vol. 242, pp. 1756–1759 (1967).
Juni, Journal of Biological Chemistry, vol. 195, pp. 715–726 (1952).
Wang et al., Fermentation and Enzyme Technology, p. 51 (1979).

Primary Examiner—Lionel M. Shapiro
Attorney, Agent, or Firm—Fidelman, Wolffe & Waldron

[57] ABSTRACT

A novel alpha-acetolactate decarboxylase enzyme product with improved stability is provided. The novel enzyme is produced in high levels by cultivation of Bacillus strains selected from the group consisting of *Bacillus brevis* and *Bacillus licheniformis* ATCC 11031, ATCC 12759, ATCC 12713, ATCC 11946, ATCC 27326, NRRL B-3751, NCTC 2120, NCTC 8721, NCIB 6816, NCIB 8537 and NCIB 11868.

5 Claims, 4 Drawing Figures

ALPHA-ACETOLACTATE DECARBOXYLASE ENZYME AND PREPARATION THEREOF

This invention concerns a novel α-acetolactate decarboxylase and a process for its preparation.

INTRODUCTION

During the fermentation of alcoholic beverages e.g. beer or wine small amounts of diacetyl is often produced. Formation of diacetyl is most disadvantageous because of its strong and unpleasant smell and in case of beer even small amounts of diacetyl of about 0.10 to 0.15 mg/liter has a negative affect on the flavour and taste of the beer. Diacetyl in beer is caused partly by an infection with a Pediococcus strain which directly produces diacetyl (E. Geiger, Diacetyl in Bier, Brauwelt 46, 1680–1692, 1980) and partly by the fact that the beer yeast from pyruvate forms α-acetolactate which by a non-enzymatic, but temperature depending reaction is converted into diacetyl. During the maturation of beer diacetyl is converted into acetoin by reductases in the yeast cells. Acetoin is with respect to taste and flavour acceptable in beer in much higher concentrations than diacetyl.

Another possibility to reduce the diacetyl amount in beer is directly to convert α-acetolactate into acetoin by means of acetolactate decarboxylase, vide EP-patent application No. 46066. The acetolactate decarboxylase may be added during the main fermentation of the beer or during the maturation process.

The enzyme which is an intracellular enzyme is recovered from the microorganism *Klebsiella pneumonia* (Juni E., J.Biol.Chem. 195, 715–726, 1952). As *Klebsiella pneumonia* is a pathogenic microorganism it is, however, not well suited for industrial utilization. Furthermore, the acetolactate decarboxylase produced by this microorganism has a poor stability during the conditions of its intended use, which in case of beer is about pH 4.3 and about 10° C.

The purpose of the present invention is to provide a novel acetolactate decarboxylase enzyme having a better stability under the above conditions and which further can be recovered from non-pathogenic microorganisms in improved yields.

BRIEF STATEMENT OF THE INVENTORS

The invention resides in the surprising discovery that a novel acetolactate decarboxylase having such properties is produced in high levels by microorganisms belonging to the *Bacillus brevis* and *Bacillus licheniformis* species.

According to its first aspect the present invention provides a novel stable α-acetolactate decarboxylase enzyme obtainable by cultivation in a suitable nutrient medium of a *Bacillus brevis* strain ATCC 11031, or *Bacillus licheniformis* strains ATCC 12759, ATCC 12713, ATCC 11946, ATCC 27326, NRRL B-3751, NCTC 2120, NCTC 8721, NCIB 6816 NCIB 8537 and NCIB 11868.

The α-acetolactate decarboxylase enzyme product may be in solid or liquid form and will generally in solid form have an activity in the range of from 0.1–10 NU (as hereinafter defined) per mg protein.

Reference is now made to the attached drawings wherein.

Figure 3:
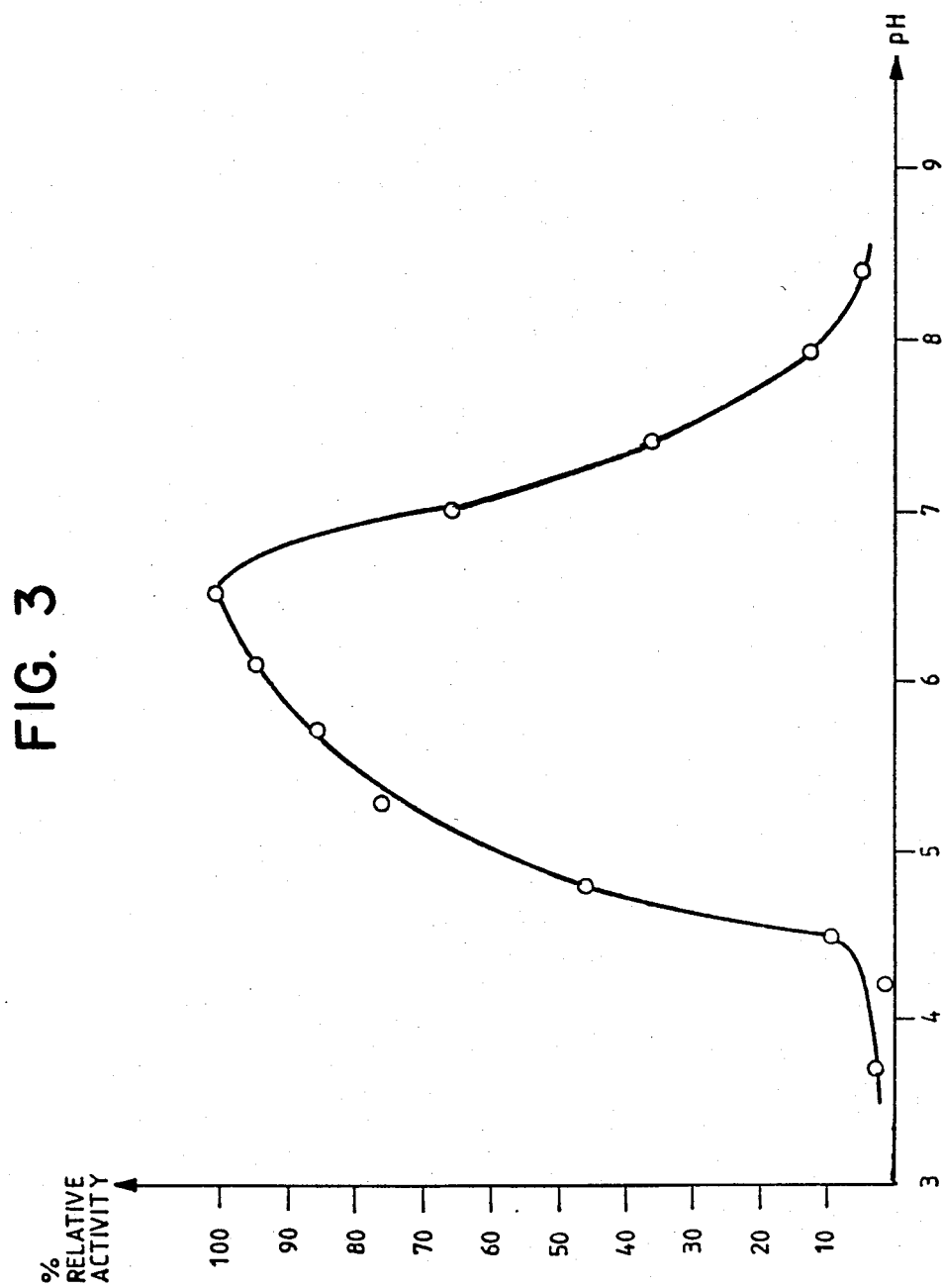
Figure 4:
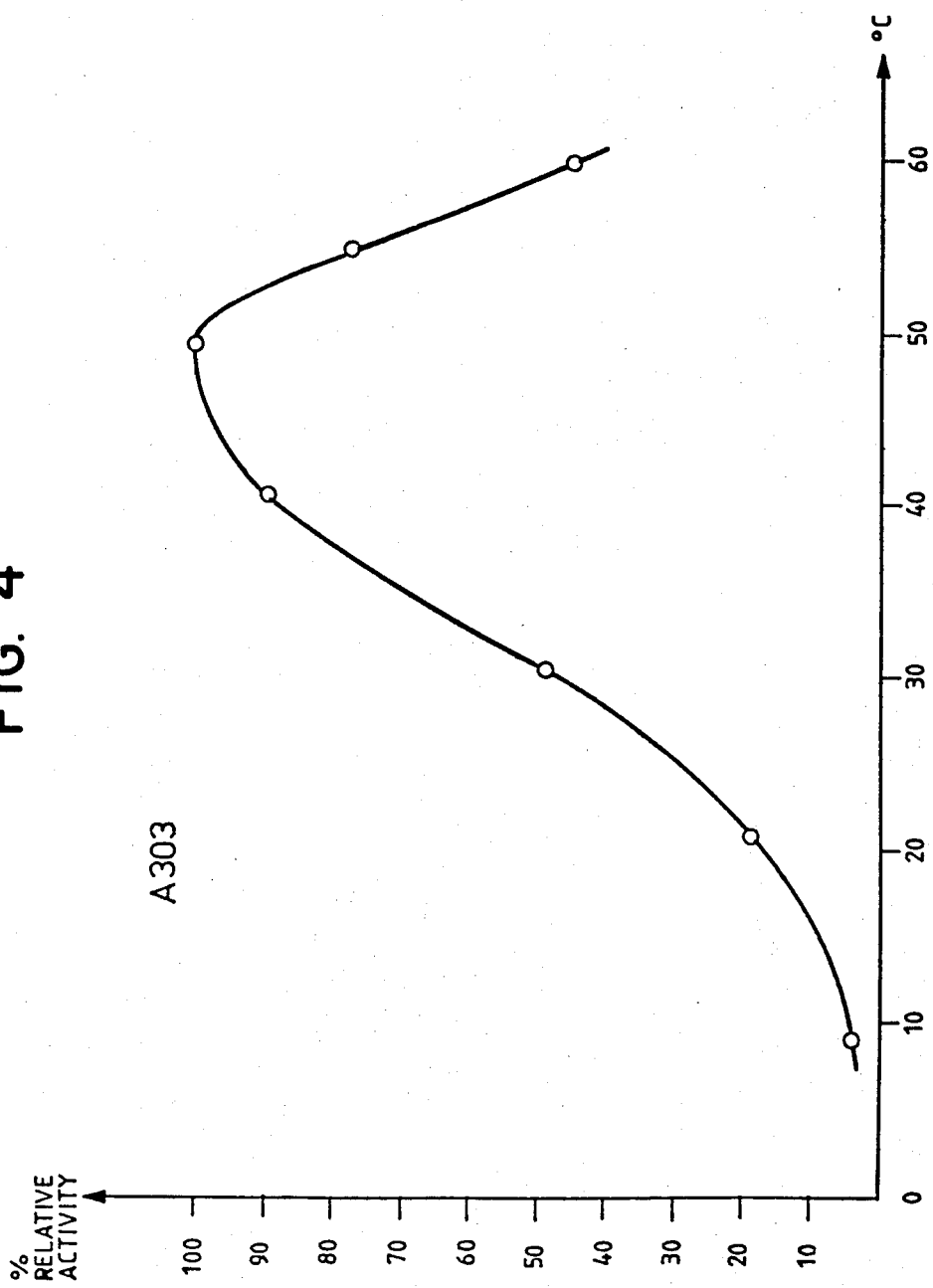

FIG. 3 graphically illustrates the relative activity at 30° C. plotted against pH; and FIG. 4 graphically illustrates the relative activity at pH 6 plotted against temperature.

According to a further aspect of the present invention there is provided a process for the preparation of an α-acetolactate decarboxylase enzyme which process comprises the cultivation in a suitable nutrient medium containing carbon and nitrogen sources and inorganic salts of an α-acetolactate decarboxylase producing Bacillus strain selected from the group consisting of *Bacillus brevis* and *Bacillus licheniformis* strains and thereafter recovery of the α-acetolactate decarboxylase enzyme from the cells in the culture medium.

In a preferred embodiment of the present invention the *Bacillus brevis* strain is ATCC 11031 or a mutant or variant thereof productive of the α-acetolactate decarboxylase enzyme.

Preferred *Bacillus licheniformis* strains are ATCC 12759, ATCC 12713, ATCC 11946, ATCC 27326, NRRL B-3751, NCTC 2120, NCTC 8721, NCIB 6816, NCIB 8537 and NCIB 11868 and mutants and variations thereof productive of the α-acetolactate decarboxylase enzyme.

When a *Bacillus licheniformis* strain is used for preparing the α-acetolactate decarboxylase enzyme of this invention the nutrient medium should preferably comprise a nitrogen source whose content of free amino acids does not repress the formation of the α-acetolactate decarboxylase, preferably an inorganic nitrogen source.

When Bacillus brevis is the source of the enzyme an organic nitrogen source could be used.

DETAILED DESCRIPTION OF THE INVENTION

The microorganisms productive of the α-acetolactate decarboxylase enzyme of the present invention were selected by means of their ability to convert α-acetolactate to acetoin which is then detected.

More than 300 Bacillus strains have been tested according to the following procedure:

The strains are cultivated in shake flasks at 30° C. and 37° C. for 24 hours on the following BCM-substrate:

$K_2HPO_4$: 1 g
$NaH_2PO_4, 2H_2O$: 1 g
$(NH_4)_2SO_4$: 2.5 g
NaCl: 0.25 g
$MgSO_4, 7H_2O$: 0.2 g
$FeCl_3, 6H_2O$: 0.04 g
$MnSO_4, H_2O$: 0.25 mg
Glucose: 10 g
Yeast extract: 3 g
Water up till: 1000 g After cultivation the cells were harvested by centrifugation, washed in 0.03M phosphate/citrate buffer (pH 6.0) and resuspended in the same buffer until OD(450)~40. Aliquots of 2 ml were then subjected to an ultrasonic treatment or treatment with 1 mg lysozyme per ml at 37° C. in 30 min. and then centrifuged.

The α-acetolactate decarboxylase activity of the supernatants were determined according to the procedure described in the paragraph "Determination of α-acetolactate decarboxylase activity".

The screening procedure revealed that only a few of the about 300 microorganisms tested produce α-acetolactate decarboxylase in detectable amounts. These microorganisms are listed in the following table I together with the enzyme activity determined according to the above procedure.

TABLE I
Result of screening procedure

| Strain | Strain (NOVO collection No.) | Activity (NU) per mg protein | Protein mg/ml |
|---|---|---|---|
| B. brevis | A 303 | 0.13 | 4 |
| B. coagulans | A 345 | 0.007 | 3 |
| B. pumilus | A 185 | 0.008 | 2 |
| B. pumilus | A 328 | 0.011 | 3 |
| B. pumilus | A 329 | 0.004 | 2 |
| B. subtilis | A 518 | 0.005 | 3 |
| B. subtilis | C 601 | 0.06 | 1 |
| B. licheniformis | A 446 | 0.11 | 3 |
| B. licheniformis | C 600 | 0.19 | 2 |
| B. licheniformis | A 88 | 0.15 | 2 |
| B. licheniformis | A 105 | 0.13 | 2 |
| B. licheniformis | A 106 | 0.15 | 2 |
| B. licheniformis | A 200 | 0.15 | 2 |
| B. licheniformis | A 203 | 0.25 | 2 |
| B. licheniformis | A 244 | 0.11 | 2 |
| B. licheniformis | A 248 | 0.14 | 2 |
| B. licheniformis | A 1240 | 0.13 | 2 |

Strains C 600 and C 601 were deposited by the applicants with the National Collection of Industrial Bacteria, Torry Research Station, Aberdeen, Scotland on May 27, 1983 and accorded the reference number NCIB 11868 and NCIB 11869, respectively.

The remaining strains were obtained from different culture collections as appears from the following list:

| NOVO No. | Deposit No. | |
|---|---|---|
| A 303 | ATCC 11031 | |
| A 345 | NRS 83 | |
| A 185 | ATCC 71 | |
| A 328 | ATCC 4520 | (B. Mesentericus var. flavus) |
| A 329 | ATCC 7065 | |
| A 518 | IAM 1109 | (B. natto) |
| A 446 | NRRL B-3751 | (Determined by the applicant to be a B. licheniformis) |
| A 88 | ATCC 12759 | |
| A 105 | ATCC 12713 | = NRRL B-1001 |
| A 106 | ATCC 11946 | |
| A 200 | NCIB 6816 | |
| A 203 | NCIB 8537 | |
| A 244 | NCTC 2120 | |
| A 248 | NCTC 8721 | |
| A 1240 | ATCC 27326 | |

The prior art (Juni E., ibid.) suggests that cell-free extracts of Bacillus subtilis are able to decarboxylate α-acetolactate to form acetoin, however, without using such extracts. The inventors hereof have tested 69 different Bacillus subtilis strains. Of these only 5 showed α-acetolactate decarboxylase activity and furthermore, these 5 strains were poor enzyme producers. Bacillus coagulans and Bacillus pumilus strains also turned out to be too poor enzyme producers for industrial application.

Of the tested Bacillus licheniformis strains 13 did not produce α-acetolactate decarboxylase in detectable amounts, 21 strains produced the enzyme in low level amounts and 11 strains (10 of which are listed in this specification) produced the enzyme in high level amounts. It was found by tandem crossed immunoelectrophoresis that all the listed Bacillus licheniformis strains produce an α-acetolactate decarboxylase enzyme immunochemical identical to that produced by Bacillus licheniformis strain C 600.

The Bacillus brevis strains have been grown on three different media in shake flasks. Only one strain, A 303 (ATCC 11031) showed α-acetolactate decarboxylase activity on all three media. The remaining 11 strains did not show α-acetolactate decarboxylase activity in detectable amounts on any of the three media used. The α-acetolactate decarboxylase enzyme produced by Bacillus brevis A 303 was found to be non identical, with respect to immunochemical properties to the enzyme produced by Bacillus licheniformis strain C 600. However, the fact that the α-acetolactate decarboxylase enzymes from the different Bacillus licheniformis strains exhibit immunochemical identity causes the inventors hereof to expect that other α-acetolactate decarboxylase producing Bacillus brevis strains than those tested by the inventors would produce essentially the same enzyme as Bacillus brevis A 303. With respect to "immunochemical identity" reference is made to N. H. Axelsen et al., "A Manual of Quantitative Immunoelectrophoresis" (Oslo 1973) chapter 10.

For the practice of this invention Bacillus brevis is preferred compared to Bacillus licheniformis because the α-acetolactate decarboxylase from Bacillus brevis is elaborated without undesirable side activities, notably ferrulic acid decarboxylase activity produced by all the tested Bacillus licheniformis strains. Ferrulic acid decarboxylase decarboxylates ferrulic acid present in fermenting beer to the extremely ill-tasting compound 4-vinylguajacol. Accordingly the ferrulic acid decarboxylase must be removed from the culture broth from Bacillus licheniformis during the recovery process.

Furthermore, Bacillus brevis is preferred as compared to Bacillus licheniformis because Bacillus brevis produces an enzyme converting the normal precursors of 2,3-pentanedion in beer to 3-hydroxy-2-pentanone thus reducing the amounts of ill-tasting pentanedions to an acceptable low level. Bacillus licheniformis strains do not produce such enzyme.

Finally, the Bacillus brevis strain gives better overall yields in the purification procedure because of lesser autolytic activity compared to Bacillus licheniformis strains.

DETERMINATION OF ALPHA-ACETOLACTATE DECARBOXYLASE ACTIVITY

One NOVO unit (NU) is defined as the amount of enzyme which produces 1 $\mu$mol acetoin per minute at 20° C. and pH 6.0 (0.03 molar citrate/phosphate buffer for the Bacillus licheniformis enzyme and a buffer system of 0.05M MES (2(N-morpholino)-ethane sulphonic acid), 0.5 mM $MgCl_2$ and 0.86M NaCl for the Bacillus brevis enzyme) by incubation of an enzyme containing test sample with an α-acetolactate substrate in the following assay:

SUBSTRATE

The α-acetolactate substrate was prepared immediately before use by hydrolysis of alpha-acetoxyalpha-methyl-acetic acid ethylester:

30 μl of diester (0.165 m mol), 240 μl of water and 330 μl of 1M NaOH was mixed and stored on ice for 15 min. 5.4 ml of water was then added and the obtained hydrolysate was used for the test.

ASSAY

Buffer and test samples with an enzyme activity of about 0.006–0.3 NU were mixed and temperated at 20° C. for a few minutes (final volume 10.0 ml). At t=0 400 μl hydrolyzate was added and samples of 1 ml were taken at t=3, 6, 9, 20 and 50 min. The enzyme reaction was stopped by placing the samples on ice and additing of 200 μl 1M NaOH.

The amount of acetoin formed is measured according to W. W. Westerfeld (A Colorimetric Determination of Blood Acetoin, J.Biol.Chem. 161, 495–502, 1945) by addition of 0.2 ml 0.5% creatin and 0.2 ml 5% alpha-naphthol in 2.5N NaOH (freshly prepared) to 1.2 ml of the above samples. After 60 min. reaction time E(524) was measured.

As blank a sample with a buffer instead of cell extract was used.

A standard curve is plotted with 0, 0.5, 2 and 4 μg/ml acetoin.

PREPARATION OF ALPHA-ACETOLACTATE DECARBOXYLASE ENZYME PRODUCT

A Bacillus strain capable of producing the α-acetolactate decarboxylase enzyme of the present invention is usually propagated in a suitable solid nutrient medium at about 30° C. prior to its cultivation under aerobic conditions in a suitable fermentation medium. The fermentation medium contains assimilable sources of carbon (e.g. dextrose) and a basal salt composition comprising e.g. ammonium sulphate as the nitrogen source. It is essential for obtaining high yields in the *Bacillus licheniformis* system that the fermentation medium does not contain excess of free amino acids which can repress the α-acetolactate decarboxylase production. In the *Bacillus brevis* system this is not the case. The fermentation is conducted at about 30° C. and at about pH 7, which is kept approximately constant by automatic means. Aerating and stirring is adjusted to obtain a positive oxygen pressure.

After fermentation the cells are harvested by centrifugation and washed in a suitable buffer. The cells are lysed by ultrasonic treatment, French press treatment, lysozyme treatment, Manton-Gaulin-processing or a combination hereof.

After centrifugation a crude extract is obtained which may be subjected to a purification step as described in the following paragraph.

PURIFICATION OF ALPHA-ACETOLACTATE DECARBOXYLASE ENZYME

The α-acetolactate decarboxylase enzyme of the present invention may be purified from the crude extract by combination of one or more of the following steps:

(a) ammonium sulphate precipitation
(b) polyethylene glycol precipitation
(c) DE 52-anion exchange chromatography and dialysis,
(d) acid precipitation and dialysis,
(e) hydroxyapatite chromatography and dialysis and
(f) lyophilization
(g) phenyl-sepharose chromatography
(h) chromatofocusing Purification of α-acetolactate decarboxylase obtained from cultivating a Bacillus licheniformis strain C 600 cultivated as described in Example 1 was performed as follows:

94 g of cells (wet weight) were suspended in 20 mM of K-phosphate buffer pH 6.8 and lysozyme treated for 30 min. with 1 mg/ml lysozyme at 37° C. and then treated with ultra sound on a Branson sonifier B 12. After centrifugation the supernatant was applied to a DE 52 anion exchanger column whereby the enzyme was completely adsorbed. The column was washed with 20 mM potassium phosphate buffer (pH 6.8) and eluted with a potassium phosphate gradient (20 mM–500 mM) pH 6.8. The fractions were analysed for enzyme activity as described above. Activity containing fractions were pooled.

The pooled fractions were acid precipitated by addition of phoshoric acid until pH 4.5. After centrifugation the supernatant was dialyzed against 20 mM potassium phosphate pH 6.8. The dialyzate was applied to a hydroxyapatite (HA) column which after wash with potassium phosphate buffer pH 6.8 was eluted with a potassium phosphate gradient as above.

The fractions exhibiting enzyme activity were pooled and dialyzed overnight against 20 mM potassium phosphate pH 6.8. Finally, the dialyzate was lyophilized.

The enzyme activity and yields appear from the following table:

TABLE II

Purification of 94 g (wet weight) of cells from culturing of strain C 600

| Fraction | Volume ml | Protein mg | NU per ml | NU total | NU per mg protein | Purification factor | Yield % |
|---|---|---|---|---|---|---|---|
| Crude extract | 360 | 12168 | 0.838 | 302 | 0.025 | 1 | 100 |
| Pool after DE 52 | 270 | 3510 | 1.431 | 386 | 0.110 | 4.4 | 128 |
| Pool after acid precipitation | 300 | 810 | 1.450 | 435 | 0.537 | 21.5 | 144 |
| After dialysis | 300 | 660 | 1.236 | 371 | 0.562 | 22.5 | 123 |
| Pool after HA-chromatography | 225 | 491 | 1.226 | 276 | 0.562 | 22.5 | 91 |
| After dialysis | 245 | 488 | 1.184 | 290 | 0.594 | 23.8 | 96 |

TABLE II-continued

| Purification of 94 g (wet weight) of cells from culturing of strain C 600 | | | | | | |
|---|---|---|---|---|---|---|
| Fraction | Volume ml | Protein mg | NU per ml | NU total | NU per mg protein | Purification factor | Yield % |
| Powder | 1.08 g | 389 | | 315 | 0.810 | 32.4 | 104 |

ENZYME CHEMICAL PROPERTIES

Figure 1:
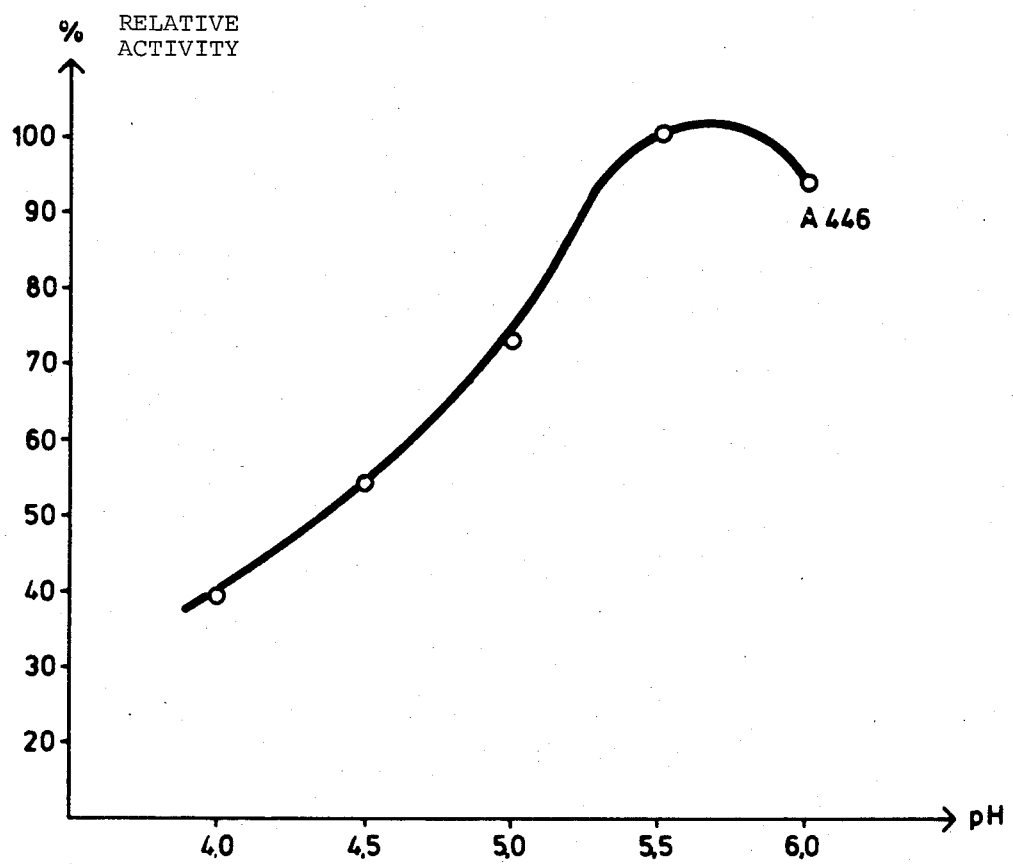
FIG. 1 shows relative activity plotted against pH for the α-acetolactate decarboxylase of Bacillus licheniformis strain A-466.
Figure 2:
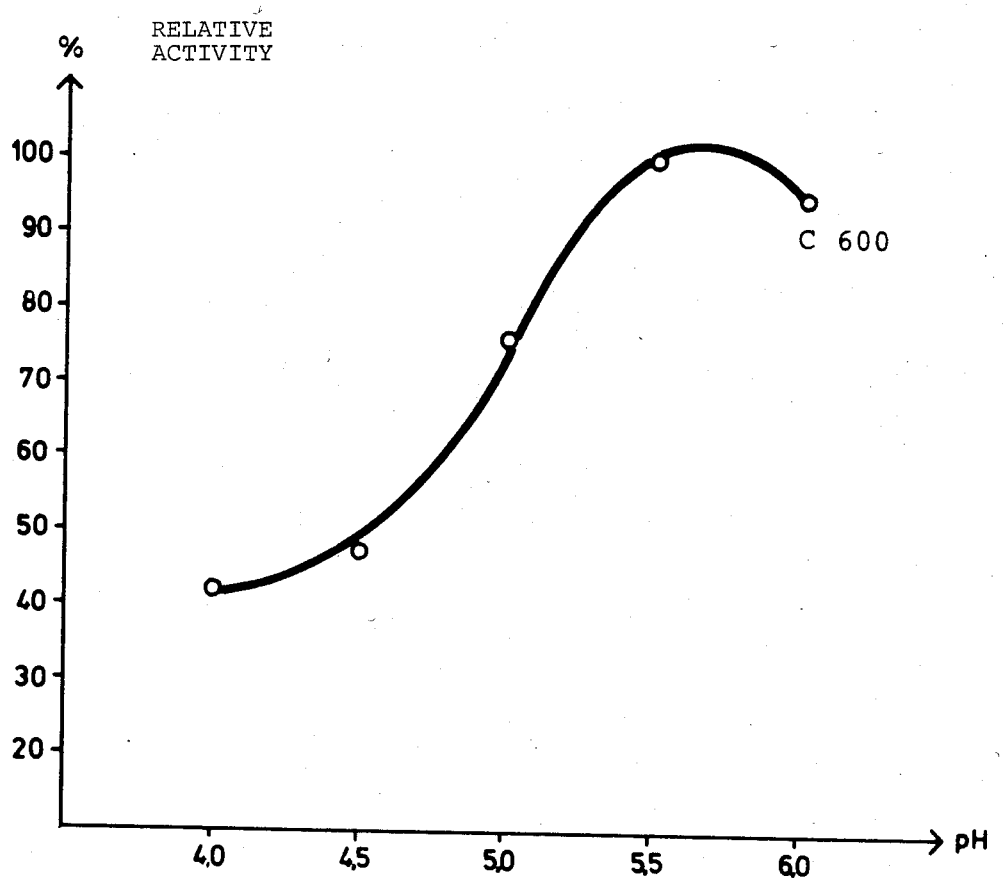
FIG. 2 shows relative activity plotted against pH for the α-acetolactate decarboxylase of Bacillus licheniformis strain C-600.

The dependence of the activity of the *Bacillus licheniformis*-acetolactate decarboxylase enzyme of the present invention on pH was determined on extracts of *Bacillus licheniformis* strains A 446 and C 600 at different pH values in 0.03M citrate/phosphate buffer at 20° C. by the method for determination of α-acetolactate decarboxylase activity above. Reference is made to the attached drawings in which FIG. 1 and FIG. 2 graphically illustrate the relative activity plotted against pH for the α-acetolactate decarboyxlase enzyme prepared from the strains A 446 and C 600, respectively. The pH optimum was found to be in the range of 5–6.

The pH and temperature dependence of the activity of the *Bacillus brevis* α-acetolactate decarboxylase was determined on an extract of *Bacillus brevis* strain A 303 by the same procedure as described above with the only exception that the buffer system used consists of 0.005M MES (2(N-morpholino)-ethane sulphonic acid)
0.5 mM MgCl$_2$
0.86M NaCl
pH 6.0

Reference is now made to the attached drawing in which

FIG. 3 graphically illustrates the relative activity at 30° C. plotted against pH and FIG. 4 graphically illustrates the relative activity at pH 6 plotted against temperature.

The pH optimum of the Bacillus brevis enzyme was found to be in the range of 5–7 and the temperature optimum was found to be in the range of 35°–55° C.

STABILITY

The stability of the crude extracts of the *Bacillus licheniformis* enzyme were tested under the condition of use, i.e. at 10° C. and in fermented, but not maturated beer.

The stability appears from the following table.

TABLE III

| | Stability test |
|---|---|
| Strain | Half life in days |
| A 303 | 11 |
| A 446 | 21 |
| C 600 | 15 |
| A 446 | 11.5 (determined in fermenting beer) |

As the *Klebsiella pneumonia* enzyme has a half life of only 2–3 hours the enzyme according to present invention shows a considerably improved stability under the condition of use for beer brewing as compared to the known enzyme.

The stability of the *Bacillus brevis* A 303 enzyme appears from the following tables IV and V:

TABLE IV

| Residual activity (NU/ml) after incubation at different temperatures | | | |
|---|---|---|---|
| | Incubation time | Residual activity (NU/ml) Temperature | | |
| | (hours) | 30° C. | 40° C. | 50° C. |
| 0.05 M MES, pH 6.4 + 10$^{-3}$ M Mg$^{++}$ | 0 | 5.3 | | |
| | 1 | 5.2 | 4.8 | 4.1 |
| | 2 | 4.8 | 5.3 | 3.4 |
| | 4 | 4.7 | 4.0 | 0.2 |
| 0.05 M acetate, pH 4.8 + 10$^{-3}$ M Mg$^{++}$ | 0 | 5.1 | | |
| | 1 | 4.9 | 4.4 | 3.6 |
| | 2 | 5.5 | 3.7 | 3.9 |
| | 4 | 5.8 | 3.3 | 3.7 |

TABLE V

| Residual activity in NU/ml after incubation at 50° C. with varying Mg$^{++}$-concentrations | | | | | |
|---|---|---|---|---|---|
| | | Residual activity (NU/ml) | | | |
| | Incubation time (hours) | No addition of Mg$^{++}$ | 10$^{-3}$ M Mg$^{++}$ | 10$^{-2}$ M Mg$^{++}$ | 10$^{-2}$ M EDTA |
| 0.05 M MES, pH 6.5 | 0 | 5.7 | 6.2 | 5.8 | 5.8 |
| | 1 | 4.8 | 5.2 | 5.0 | 1.4 |
| | 2 | 4.2 | 4.6 | 3.3 | 0.3 |
| | 4 | 0.5 | 0.4 | 0.2 | 0 |
| 0.05 M acetate, pH 4.5 | 0 | 6.0 | 6.2 | 6.5 | 5.8 |
| | 1 | 5.3 | 5.6 | 5.8 | 0.1 |
| | 2 | 5.2 | 5.0 | 5.3 | 0 |
| | 4 | 4.9 | 5.1 | 5.8 | 0 |

It appears from the above that the *Bacillus brevis* enzyme retains from about 60 to 90% of its activity after 2 hours the enzyme being more stable at pH 4.5. Furthermore, Mg$^{++}$ ions have a stabilizing effect on the activity, whereas the enzyme is inactivated by EDTA.

pI-DETERMINATION pI has been determined on a crude extract of the strain A 446 by thin layer gelelectrofocusing to be of about 4.7.

The pI of the *Bacillus brevis* A 303 enzyme was found to be 7.6 and 7.0 determined by the chromatofocusing technique described by PHARMACIA (PHARMACIA TECHNICAL BULLETIN: CHROMATOFOCUSING with POLYBUFFER TM and PBE TM; PHARMACIA FINE CHEMICALS). The activity eluates as two peaks indicating that the α-acetolactate decarboxylase activity may consist of two proteins with different pI.

Km-DETERMINATION

Km has been determined for A 303 on α-acetolactate (DL) in non-matured beer at 10° C. to be 3.8 mM.

IMMUNOLOGICAL PROPERTIES

A purified fraction of α-acetolactate decarboxylase from strain C 600 (*Bacillus licheniformis*) was used to immunize rabbits according to the procedure described by Harboe and Ingild in: N. H. Axelsen: Handbook of Immunoprecipitation-in-Gel Techniques, Blackwell Scientific Publications. London 1983.

The antibody produced in this way against the *Bacillus licheniformis* enzyme was used to perform crossed immunoelectrophoresis and tandem crossed immunoelectrophoresis as described by A. O. Grubb and J. Kroll, respectively in the above mentioned publication.

As the antigen is not homogenous, the produced antibody is polyspecific and produces up to 15 bands in crossed immunoelectrophoresis one of which is the α-acetolactate decarboxylase precipitation band. To identify this band an overlayer technique based on enzyme activity was applied: after immunoelectrophoresis the plate was not fixed and stained as usual, but was incubated for 5 minutes in 30 ml of the following mixture in the lid of a 14 cm φ petri dish:

| 150 μl ethyl-2-acetoxy-2-methyl-acetoacetat<br>1200 μl $H_2O$<br>1650 μl 1N NaOH | Mixed and incubated at room temperature for 15 minutes. Then $H_2O$ was added to make up to 30 ml. |
|---|---|

After incubation, the mixture was allowed to drip off the plate, which was wrapped in Vitawrap plastic foil and in aluminum foil and incubated for 30 minutes at room temperature.

The plate was then placed in the lid of a 14 cm φ petri dish and covered with the following mixture:

| 30 ml 2% LSA agarose ($H_2O$)<br>3 ml 1% creatin ($H_2O$)<br>6 ml 5% Naphtol in 2.5 N NaOH | Mixed at 55° C. |
|---|---|

The covered plate was incubated at room temperature for about 1 hour. The band with the α-acetolactate decarboxylase precipitate shows a red colour, and can be identified.

As mentioned above tandem crossed immunoelectrophoresis of the enzymes from all the listed *Bacillus licheniformis* strains against C 600 α-acetolactate decarboxylase antibody revealed that the *Bacillus licheniformis* enzymes are immunochemical identical whereas the α-acetolactate decarboxylase from *Bacillus brevis* does not precipitate with C 600 α-acetolactate decarboxylase antibody demonstrating that *Bacillus licheniformis* and *Bacillus brevis* strains produce different types of the α-acetolactate decarboxylase enzyme both, however, being well suited for the intended use in beer production.

The following examples are presented as illustrative embodiments of this invention and are not intended as specific limitations thereof.

EXAMPLE 1

The strain A 446 (B. Licheniformis, NRRL B-3751) was propagated on a TY-medium in shake flasks at 30° C. until OD(450)6.

TY-medium:
Trypticase: 20 g
Yeast extract: 5 g
$FeCl_3,6H_2O$: 7 mg
$MnCl_2,4H_2O$: 1 mg
$MgSO_4,7H_2O$: 15 mg
Distilled water up to: 1000 ml 100 ml of the shake flask culture was transferred to a 1.5 liter Kieler-fermentor containing an inorganic salt medium which contains per liter:

$CaCl_2,2H_2O$: 0.5 g
$MgSO_4,7H_2O$: 0.5 g
$KH_2PO_4$: 4.0 g
$(NH_4)_2SO_4$: 22 g
Trace metals sol.*: 3 ml
Pluronic: 1 ml
Dextrose: 150 g

*Trace metals sol:
$H_3BO_3$: 500 mg/100 ml
$CuSO_4,5H_2O$: 63 mg/100 ml
KI: 100 mg/100 ml
$FeCl_3,6H_2O$: 333 mg/100 ml
$MnSO_4,H_2O$: 448 mg/100 ml
$NaMoO_4,2H_2O$: 200 mg/100 ml
$ZnSO_4,7H_2O$: 712 mg/100 ml During the cultivation pH was kept at 7.0 by addition of NaOH. The temperature was 30° C. and aerating and stirring was adjusted to obtain a positive oxygen pressure.

The cells were harvested by centrifugation after a cell density corresponding to OD(450) 34 was reached.

The progress of the fermentation appears from the following table:

TABLE VI

| Activity measured during fermentation | | |
|---|---|---|
| Fermentation time in hours | NU/ml culture | OD(450) |
| 0 | 0 | 1.35 |
| 5 | 0 | 1.69 |
| 21 | 0.022 | 19 |
| 24 | 0.076 | 28 |
| 28 | 0.440 | 34 |

EXAMPLE 2

Bacillus strain A 446 was propagated and cultivated as described in example 1 with the exception that the fermentation medium contained 180 g dextrose and that the cells were harvested when a cell density corresponding to OD (450)∼47 was reached.

112 g cells (wet weight) were suspended in 20 mM K-phosphate buffer pH 6.8 and lysozyme treated for 30 min. with 1 mg/ml lysozyme at 37° C. Then the lysed cells were subjected to an ultrasonic treatment in a Branson sonifier B 12. Ammonium sulphate was added to the obtained crude extract until 25% saturation and the mixture was placed on ice for 30 min.

After centrifugation the activity was found in the supernatant.

Ammonium sulphate was added to the supernatant until 70% saturation and the mixture was placed on ice for 30 min. After centrifugation the activity was found in the precipitate.

The precipitate was suspended in 20 mM K-phosphat pH 6.8 and then 200 mg/ml polyethylene glycol (MW 6000) was added. The mixture was left for 30 min. at room temperature. The activity was found in the supernatant after centrifugation.

The protein content in the supernatant was adsorbed on a Whatman DE 52 anion exchanger which was then washed with 20 mM K-phosphate buffer pH 6.8 and then eluated with a K-phosphate buffer gradient (20 mM–500 mM) pH 6.8. The fractions containing enzyme activity were pooled and dialyzed against 20 mM K-phosphate buffer pH 6.8. Finally the dialyzate was lyophilized.

The progress of purification procedure appears from the following table VII:

TABLE VII

| Fraction | Volume ml | Protein mg | NU per ml | NU total | NU per mg protein | Purification factor | Yield % (apparent) |
|---|---|---|---|---|---|---|---|
| Crude extract before centrifugation | 460 | 14536 | 0.496 | 228 | 0.016 | 1 | 100 |
| Supernatant after first ammonium sulphate-precipitation | 460 | 12190 | 1.053 | 484 | 0.040 | 2.5 | 212 |
| Resuspended precipitate after second ammonium sulphate-precipitation | 460 | 11638 | 1.487 | 684 | 0.059 | 3.7 | 300 |
| Supernatant after PEG-6000 precipitation | 550 | 5753 | 1.301 | 716 | 0.124 | 7.8 | 315 |
| Pool after DE 52 chrom. | 240 | 1392 | 0.955 | 229 | 0.165 | 10.3 | 100 |
| Pool after dialysis | 250 | 1275 | 0.934 | 234 | 0.183 | 11.4 | 103 |
| Powder | 2.1 g | 1218 | | 176 | 0.144 | 9.0 | 77 |

EXAMPLE 3

Strain A 303 (*Bacillus brevis*, ATCC 11031) was propagated on a TY medium (see example 1) in shake flasks at 30° C. until the cells were in the mid-logarithmic phase. 600 ml of this culture were transferred to a Biotec-fermentor which contained 8 liters of the following medium:

$(NH_4)_2SO_4$: 2.5 g/liter
$K_2HPO_4$: 1 -
$NaH_2PO_4, 2H_2O$: 1 -
NaCl: 0.25 -
$ZnSO_4, 7H_2O$: 0.125 -
$MgSO_4, 7H_2O$: 0.125 -
Trace metals sol.*: 0.7 ml/liter
Yeast extract: 6 g/liter
Pluronic: 0.13 ml/liter
Dextrose: 31.25 g/liter
(*) as described in example 1.

During cultivation, pH was kept at 7.0 by addition of NaOH, The temperature was 35° C. and stirring and aeration was adjusted to obtain a positive oxygen pressure. At the optimal time the cells were harvested by centrifugation.

The progress of the fermentation appears from the following table:

TABLE VIII

| Activity measured during fermentation | | |
|---|---|---|
| Fermentation time in hours | NU/ml culture | $OD_{450}$ |
| 1 | 0.005 | 2.4 |
| 2 | 0.01 | 4.1 |
| 3 | 0.02 | 7.5 |
| 4 | 0.18 | 15.3 |
| 5 | 0.47 | 17.5 |
| 6 | 0.41 | 22.2 |
| 7 | 0.17 | 24.0 |
| 8 | 0.13 | 24.0 |

EXAMPLE 4

Strain A 303 (*Bacillus brevis*) was propagated and cultivated as described in example 3. The cells were harvested at $OD_{450}=8.0$.

The cells were suspended in 20 mM K-phosphate buffer pH 6.8 and passed through a Manton-Gaulin type homogenizer at a pressure of about 400 Bar. A fractionated precipitation of the activity with ammonium sulphate was carried out as described in example 2.

The activity containing precipitate was dissolved in the above mentioned K-phosphate buffer, dialyzed against the same buffer and finally concentrated in an Amicon pressure dialyzing cell to a protein concentration of about 10 mg/ml.

150 ml of this extract was the starting material for the following purification procedure, as shown in table IX.

150 ml DE52 precycled ion exchanger equilibrated in 20 mM K-phosphate buffer pH 6.8 was added to the extract.

The slurry was filtrated on a Büchner funnel. The activity was in the filtrate, which was dialyzed against 25 mM Histidine-HCL buffer pH 6.2.

To this extract 40 ml PBE94 (Pharmacia chromatofocusing agent) equilibrated in the above mentioned Histidine buffer was added. The slurry was filtrated on a Büchner funnel. The activity was in the filtrate, which was dialyzed against 20 mM K-phosphate pH 6.8, 20% saturated with ammoniumsulphate. A column was packed with 200 ml phenylsepharose equilibrated in this buffer. The activity in the dialyzed filtrate was applied to the column and eluted by a gradient in 20 mM K-phosphate pH 6.8 going from 20% saturation to 0% saturation of ammonium sulphate and from 0% ethylenglycol to 50% ethylenglycol.

The activity peak was found, pooled, concentrated, and dialyzed against 20 mM K-phosphate pH 6.8, and was stored frozen.

TABLE IX

| Fraction | Vol. ml | Protein mg | Activity NU per ml | NU total | NU per mg protein | Purification factor | Yield % (apparent) |
|---|---|---|---|---|---|---|---|
| Extract | 150 | 1890 | 2.4 | 365 | 0.19 | 1 | 100 |
| Filtrate after DE52 treatment | 140 | 510 | 1.9 | 262 | 0.51 | 2.7 | 72 |
| Filtrate | 135 | 263 | 2.02 | 273 | 1.04 | 5.4 | 75 |

TABLE IX-continued

| Fraction | Vol. ml | Protein mg | Activity NU per ml | Activity NU total | NU per mg protein | Purification factor | Yield % (apparent) |
|---|---|---|---|---|---|---|---|
| after PBE94 treatment | | | | | | | |
| Pool after phenylsepharose treatment | 165 | 25 | 0.95 | 157 | 6.3 | 32 | 43 |
| Pool after concentration and dialyzing | 34 | 4.8 | 4.7 | 158 | 33 | 171 | 43 |

We claim:

1. An alpha-acetolactate decarboxylase enzyme obtained by cultivation in a suitable nutrient medium of a Bacillus brevis strain or a Bacillus licheniformis strain productive of an alpha-acetolactate decarboxylase characterized by a half-life of at least about 11 days at 10° C. in beer.

2. An alpha-acetolactate decarboxylase preparation according to claim 1 containing an alpha-acetolactate decarboxylase activity in the range of from 0.1 to 10 NU per mg protein.

3. A process for the preparation of an alpha-acetolactate decarboxylase enzyme, which process comprises cultivation in a suitable nutrient medium containing carbon and nitrogen sources and inorganic salts of an alpha-acetolactate decarboxylase producing Bacillus strain selected from the group consisting of Bacillus brevis ATCC 11031, Bacillus licheniformis ATCC 12759, ATCC 12713, ATCC 11946, ATCC 27326, NRRL B-3751, NCTC 2120, NCTC 8721, NCIB 6816, NCIB 8537, NCIB 11868 and mutants and variations thereof productive of the alpha-acetolactate decarboxylase enzyme, and thereafter recovery of the alpha-acetolactate decarboxylase enzyme from the cells in the medium.

4. A process according to claim 3 wherein the Bacillus is a Bacillus licheniformis strain and the nutrient medium comprises a nitrogen source whose content of free amino acids does not repress the formation of the alpha-acetolactate decarboxylase.

5. A process according to claim 4 wherein the nitrogen source is an inorganic nitrogen source.

* * * * *